(12) United States Patent
Schneider et al.

(10) Patent No.: US 10,471,238 B2
(45) Date of Patent: Nov. 12, 2019

(54) SERRATION BALLOON

(71) Applicant: Cagent Vascular, LLC, Wayne, PA (US)

(72) Inventors: Peter Schneider, Honolulu, HI (US); Robert M. Giasolli, Orange, CA (US)

(73) Assignee: Cagent Vascular, LLC, Wayne, PA (US)

( * ) Notice: Subject to any disclaimer, the term of this patent is extended or adjusted under 35 U.S.C. 154(b) by 160 days.

(21) Appl. No.: 15/523,936

(22) PCT Filed: Nov. 3, 2015

(86) PCT No.: PCT/US2015/058847
§ 371 (c)(1),
(2) Date: May 2, 2017

(87) PCT Pub. No.: WO2016/073490
PCT Pub. Date: May 12, 2016

(65) Prior Publication Data
US 2017/0333686 A1    Nov. 23, 2017

Related U.S. Application Data

(60) Provisional application No. 62/074,586, filed on Nov. 3, 2014.

(51) Int. Cl.
*B32B 41/00* (2006.01)
*A61M 25/10* (2013.01)
(Continued)

(52) U.S. Cl.
CPC ...... *A61M 25/1029* (2013.01); *A61M 25/104* (2013.01); *B29C 70/72* (2013.01);
(Continued)

(58) Field of Classification Search
CPC ............ A61M 25/1029; A61M 25/104; A61M 2025/109; A61M 2025/1031; A61M 2025/1086; B29C 70/72; B29L 2031/7543
(Continued)

(56) References Cited

U.S. PATENT DOCUMENTS 3,221,746 A    12/1965 Noble
3,635,223 A    1/1972 Klieman
(Continued)

FOREIGN PATENT DOCUMENTS

EP    1604704    12/2005
EP    1809361    7/2007
(Continued)

OTHER PUBLICATIONS

International Search Report and Written Opinion for International Application No. PCT/US2015/058847, dated Feb. 23, 2016 in 12 pages.
(Continued)

*Primary Examiner* — Michael N Orlando
*Assistant Examiner* — Joshel Rivera
(74) *Attorney, Agent, or Firm* — Knobbe, Martens, Olson & Bear LLP

(57) ABSTRACT

A serration balloon can have a number of different components and can be made in a number of different manners. One or more longitudinally extending members with periodic raised wedges can be attached to a medical balloon. They can be attached with a fiber coating, a polymer coating, or other methods. A polymer matrix can be used to bond the longitudinally extending member to the surface of the balloon. The fiber coating can be, for example, a thread or mesh that secures the longitudinally extending member to the balloon. The medical balloon can be an angioplasty balloon, such as an off-the-shelf angioplasty balloon.

20 Claims, 5 Drawing Sheets

(51) Int. Cl.
  *B29C 70/72* (2006.01)
  *B29L 31/00* (2006.01)
(52) U.S. Cl.
  CPC .............. *A61M 2025/109* (2013.01); *A61M 2025/1031* (2013.01); *A61M 2025/1086* (2013.01); *B29L 2031/7543* (2013.01)
(58) Field of Classification Search
  USPC .................... 156/60, 64, 350, 351, 378, 379
  See application file for complete search history.

(56) References Cited

U.S. PATENT DOCUMENTS

| | | | |
|---|---|---|---|
| 4,465,072 A | 8/1984 | Taheri |
| 5,009,659 A | 4/1991 | Hamlin |
| 5,042,707 A | 8/1991 | Taheri |
| 5,192,291 A | 3/1993 | Pannek, Jr. |
| 5,196,024 A | 3/1993 | Barath |
| 5,209,799 A | 5/1993 | Vigil |
| 5,320,634 A | 6/1994 | Vigil et al. |
| 5,336,234 A | 8/1994 | Vigil |
| 5,411,478 A | 5/1995 | Stillabower |
| 5,417,707 A | 5/1995 | Parkola |
| 5,423,851 A | 6/1995 | Samuels |
| 5,484,411 A | 1/1996 | Inderbitzen et al. |
| 5,501,689 A | 3/1996 | Green |
| 5,569,272 A | 10/1996 | Reed |
| 5,616,149 A | 4/1997 | Barath |
| 5,665,116 A | 9/1997 | Chaisson |
| 5,681,346 A | 10/1997 | Orth |
| 5,713,860 A | 2/1998 | Kaplan et al. |
| 5,713,863 A | 2/1998 | Vigil et al. |
| 5,718,684 A | 2/1998 | Gupta |
| 5,720,726 A | 2/1998 | Marcadis et al. |
| 5,797,935 A | 8/1998 | Barath et al. |
| 5,797,951 A | 8/1998 | Mueller |
| 5,800,526 A | 9/1998 | Anderson |
| 5,868,779 A | 2/1999 | Ruiz |
| 5,957,949 A | 9/1999 | Leonhardt et al. |
| 6,007,543 A | 12/1999 | Ellis |
| 6,036,725 A | 3/2000 | Avellanet |
| 6,048,332 A | 4/2000 | Duffy et al. |
| 6,053,943 A | 4/2000 | Edwin |
| 6,102,904 A | 8/2000 | Vigil et al. |
| 6,126,685 A | 10/2000 | Lenker |
| 6,197,013 B1 | 3/2001 | Reed |
| 6,221,102 B1 | 4/2001 | Baker |
| 6,280,414 B1 | 8/2001 | Shah et al. |
| 6,290,728 B1 | 9/2001 | Phelps |
| 6,371,962 B1 | 4/2002 | Ellis |
| 6,450,989 B2 | 9/2002 | Dubrul et al. |
| 6,475,237 B2 | 11/2002 | Drasler |
| 6,562,062 B2 | 5/2003 | Jenusaitis et al. |
| 6,623,452 B2 | 9/2003 | Chien et al. |
| 6,626,861 B1 | 9/2003 | Hart et al. |
| 6,632,231 B2 | 10/2003 | Radisch, Jr. |
| 6,638,246 B1 | 10/2003 | Naimark et al. |
| 6,692,504 B2 | 2/2004 | Kurz |
| 6,719,775 B2 | 4/2004 | Slaker |
| 6,808,518 B2 | 10/2004 | Wellman et al. |
| 6,942,680 B2 | 9/2005 | Garyzel et al. |
| 7,007,698 B2 | 3/2006 | Thornton |
| 7,011,670 B2 | 3/2006 | Radisch, Jr. |
| 7,087,088 B2 | 8/2006 | Berg |
| 7,172,609 B2 | 2/2007 | Radisch, Jr. |
| 7,179,284 B2 | 2/2007 | Khosravi |
| 7,179,345 B2 | 2/2007 | Shkolnik |
| 7,186,237 B2 | 3/2007 | Meyer et al. |
| 7,211,101 B2 | 5/2007 | Carley |
| 7,252,675 B2 | 8/2007 | Wyzgala et al. |
| 7,270,673 B2 | 9/2007 | Yee |
| 7,279,002 B2 | 10/2007 | Shaw et al. |
| 7,291,158 B2 | 11/2007 | Crow |
| 7,303,572 B2 | 12/2007 | Meisheimer |
| 7,326,245 B2 | 2/2008 | Rosenthal et al. |
| 7,331,992 B2 | 2/2008 | Randall |
| 7,413,558 B2 | 8/2008 | Kelley et al. |
| 7,500,986 B2 | 3/2009 | Lye et al. |
| 7,611,484 B2 | 11/2009 | Wellman et al. |
| 7,662,163 B2 | 2/2010 | Grayzel et al. |
| 7,686,824 B2 | 3/2010 | Konstantino |
| 7,691,119 B2 | 4/2010 | Farnan |
| 7,771,447 B2 | 8/2010 | Kunis |
| 7,883,537 B2 | 2/2011 | Grayzel et al. |
| 7,931,663 B2 | 4/2011 | Farnan |
| 7,933,660 B2 | 4/2011 | Carr |
| 7,947,015 B2 | 5/2011 | Herweck et al. |
| 7,972,351 B2 | 7/2011 | Trinidad |
| 7,985,234 B2 | 7/2011 | Wang et al. |
| 7,993,358 B2 | 8/2011 | O'Brien |
| 8,002,725 B2 | 8/2011 | Hogendijk |
| 8,038,691 B2 | 10/2011 | Bence et al. |
| 8,052,703 B2 | 11/2011 | St. Martin et al. |
| 8,114,049 B2 | 2/2012 | Freyman et al. |
| 8,192,675 B2 | 6/2012 | Burton et al. |
| 8,211,354 B2 | 7/2012 | Burton |
| 8,323,243 B2 | 12/2012 | Schnieder et al. |
| 8,361,096 B2 | 1/2013 | Bence et al. |
| 8,454,637 B2 | 6/2013 | Aggerholm et al. |
| 8,491,615 B2 | 7/2013 | Manderfeld et al. |
| 8,523,887 B2 | 9/2013 | Grayzel et al. |
| 8,557,271 B2 | 10/2013 | Kimble et al. |
| 8,690,903 B2 | 4/2014 | Bence et al. |
| 9,017,353 B2 | 4/2015 | Bence et al. |
| 9,061,127 B2 | 6/2015 | Weber et al. |
| 9,066,749 B2 | 6/2015 | Burton et al. |
| 9,095,688 B2 | 8/2015 | Burton |
| 9,179,936 B2 | 11/2015 | Feld et al. |
| 9,199,066 B2 | 12/2015 | Konstantino et al. |
| 9,216,033 B2 | 12/2015 | Feld et al. |
| 9,226,768 B2 | 1/2016 | Gunderson et al. |
| 9,242,076 B2 | 1/2016 | Burton et al. |
| 9,302,071 B2 | 4/2016 | Manderfeld et al. |
| 9,320,530 B2 | 4/2016 | Grace |
| 9,339,291 B2 | 5/2016 | Aggerholm et al. |
| 9,393,386 B2 | 7/2016 | Schneider et al. |
| 9,415,193 B2 | 8/2016 | Campbell et al. |
| 9,480,826 B2 | 11/2016 | Schneider et al. |
| 9,586,031 B2 | 3/2017 | Konstantino et al. |
| 9,592,119 B2 | 3/2017 | Tilson et al. |
| 9,603,619 B2 | 3/2017 | Bence et al. |
| 9,604,036 B2 | 3/2017 | Burton et al. |
| 10,166,374 B2 | 1/2019 | Giasolli et al. |
| 2001/0016726 A1 | 8/2001 | Dubrul et al. |
| 2001/0020151 A1 | 9/2001 | Reed et al. |
| 2002/0010489 A1 | 1/2002 | Grayzel et al. |
| 2002/0077594 A1 | 6/2002 | Chien et al. |
| 2003/0065303 A1 | 4/2003 | Wellman et al. |
| 2003/0153870 A1 | 8/2003 | Meyer et al. |
| 2003/0158595 A1 | 8/2003 | Randall |
| 2003/0163148 A1 | 8/2003 | Wang et al. |
| 2004/0098014 A1 | 5/2004 | Flugelman et al. |
| 2004/0106904 A1 | 6/2004 | Gonnelli et al. |
| 2004/0143287 A1 | 7/2004 | Konstantino et al. |
| 2004/0158270 A1 | 8/2004 | Wyzgala et al. |
| 2004/0186551 A1 | 9/2004 | Kao |
| 2004/0249445 A1 | 12/2004 | Rosenthal et al. |
| 2005/0021070 A1 | 1/2005 | Feld et al. |
| 2005/0137618 A1 | 6/2005 | Kunis |
| 2005/0149082 A1 | 7/2005 | Yee et al. |
| 2005/0177130 A1 | 8/2005 | Konstantino et al. |
| 2005/0203388 A1 | 9/2005 | Carr |
| 2005/0251164 A1 | 11/2005 | Gifford |
| 2005/0267409 A1 | 12/2005 | Shkolnik |
| 2005/0288764 A1 | 12/2005 | Snow |
| 2006/0085023 A1 | 4/2006 | Davies et al. |
| 2006/0122684 A1 | 6/2006 | Lye et al. |
| 2006/0149308 A1 | 7/2006 | Melsheimer |
| 2006/0271093 A1 | 11/2006 | Holman |
| 2007/0016232 A1* | 1/2007 | St. Martin ...... A61B 17/320725 606/159 |
| 2007/0021774 A1 | 1/2007 | Hogendijk |
| 2007/0093744 A1 | 4/2007 | Elmaleh |
| 2007/0191766 A1 | 8/2007 | McMorrow |

(56) References Cited

U.S. PATENT DOCUMENTS

| | | |
|---|---|---|
| 2007/0191811 A1 | 8/2007 | Berglund |
| 2007/0213761 A1 | 9/2007 | Murphy et al. |
| 2008/0015500 A1 | 1/2008 | Herweck et al. |
| 2009/0157159 A1 | 6/2009 | Schneider et al. |
| 2009/0214615 A1 | 8/2009 | Zhao |
| 2009/0227949 A1 | 9/2009 | Knapp et al. |
| 2009/0240270 A1 | 9/2009 | Schneider et al. |
| 2010/0015196 A1 | 1/2010 | Kimble et al. |
| 2010/0042121 A1 | 2/2010 | Schneider et al. |
| 2010/0087783 A1* | 4/2010 | Weber ............. A61L 27/34 604/103.02 |
| 2010/0274188 A1 | 10/2010 | Chang et al. |
| 2010/0274271 A1* | 10/2010 | Kelley ........ A61B 17/320725 606/159 |
| 2011/0178503 A1 | 7/2011 | Kangas |
| 2012/0041412 A1 | 2/2012 | Roth et al. |
| 2012/0059401 A1 | 3/2012 | Konstantino et al. |
| 2012/0172901 A1 | 7/2012 | Manderfled et al. |
| 2012/0277843 A1 | 11/2012 | Weber et al. |
| 2013/0018396 A1* | 1/2013 | Gunderson .... A61B 17/320725 606/159 |
| 2013/0066346 A1 | 3/2013 | Pigott |
| 2013/0165958 A1 | 6/2013 | Schneider et al. |
| 2013/0211381 A1 | 8/2013 | Feld |
| 2013/0218181 A1 | 8/2013 | Feld et al. |
| 2013/0253426 A1 | 9/2013 | Campbell et al. |
| 2013/0261545 A1 | 10/2013 | Osypka |
| 2014/0066898 A1 | 3/2014 | Cully et al. |
| 2014/0066960 A1 | 3/2014 | Feld et al. |
| 2016/0081711 A1 | 3/2016 | Gunderson et al. |
| 2016/0175568 A1 | 6/2016 | Manderfeld et al. |
| 2016/0324538 A1 | 11/2016 | Schneider et al. |
| 2017/0100570 A1 | 4/2017 | Giasolli et al. |
| 2017/0112526 A1 | 4/2017 | Burton et al. |
| 2017/0150988 A1 | 6/2017 | Konstantino et al. |
| 2018/0200491 A1 | 7/2018 | Giasolli et al. |
| 2018/0304052 A1 | 10/2018 | Schneider et al. |

FOREIGN PATENT DOCUMENTS

| | | |
|---|---|---|
| JP | H09-108358 | 4/1997 |
| JP | H09-192226 | 7/1997 |
| JP | 2006501869 | 1/2006 |
| WO | WO 2002/043796 | 6/2002 |
| WO | WO 2002/078511 | 10/2002 |
| WO | WO 2003/051442 | 6/2003 |
| WO | WO 2003/101310 | 12/2003 |
| WO | WO 2006/130194 | 12/2006 |
| WO | WO 2008/020980 | 2/2008 |
| WO | WO 2009/117158 | 9/2009 |
| WO | WO 2015/187872 | 12/2015 |
| WO | WO 2016/073490 | 5/2016 |
| WO | WO 2016/073511 | 5/2016 |
| WO | WO 2018/094077 | 5/2018 |

OTHER PUBLICATIONS

Supplemental Search Report for European Application No. 15857951.6, dated Jun. 7, 2018 in 7 pages.

\* cited by examiner

SERRATION BALLOON

INCORPORATION BY REFERENCE TO ANY PRIORITY APPLICATIONS

This application is the U.S. National Stage of PCT/US2015/058847 filed on Nov. 3, 2015, which in turn claims priority to U.S. Provisional App. No. 62/074586 filed Nov. 3, 2014. All of the above application(s) is/are incorporated by reference herein in their entirety and are to be considered a part of this specification. Any and all applications for which a foreign or domestic priority claim is identified in the Application Data Sheet as filed with the present application are hereby incorporated by reference under 37 CFR 1.57.

BACKGROUND

Field of the Invention

Certain embodiments disclosed herein relate generally to a medical balloon, for example a medical cutting or serration balloon. Particular embodiments disclose features of a medical balloon such as an angioplasty balloon having adjustable outer dimensions, surface protrusions, and methods of controlled tearing of plaque during an angioplasty procedure.

Description of the Related Art

Atherosclerotic occlusive disease is the primary cause of stroke, heart attack, limb loss, and death in the US and the industrialized world. Atherosclerotic plaque forms a hard layer along the wall of an artery and is comprised of calcium, cholesterol, compacted thrombus and cellular debris. As the atherosclerotic disease progresses, the blood supply intended to pass through a specific blood vessel is diminished or even prevented by the occlusive process. One of the most widely utilized methods of treating clinically significant atherosclerotic plaque is balloon angioplasty.

Balloon angioplasty is a method of opening blocked or narrowed blood vessels in the body. The balloon angioplasty catheter is placed into the artery from a remote access site that is created either percutaneously or through open exposure of the artery. The catheter is typically passed along the inside of the blood vessel over a wire that guides the way of the catheter. A portion of the catheter with a balloon attached is placed at the location of the atherosclerotic plaque that requires treatment. The balloon is inflated, generally to a size consistent with the original diameter of the artery prior to developing occlusive disease.

When the balloon is inflated, the plaque may be stretched, compressed, fractured, and/or broken, depending on its composition, location, and the amount of pressure exerted by the balloon. Plaque can be heterogeneous and may be soft in some areas or hard in others causing unpredictable cleavage planes to form under standard balloon angioplasty. Balloon angioplasty can cause plaque disruption and sometimes it causes arterial injury at the angioplasty site. There is a continuing need to improve the methods and systems for treating occlusive disease, including balloon angioplasty methods and systems.

SUMMARY OF THE INVENTION

A cutting or serration balloon can have a number of different components and can be made in a number of different manners. For example, one or more longitudinally extending members with periodic raised wedges can be attached to a medical balloon. They can be attached with a fiber coating, a polymer coating, or other methods. The fiber coating can be, for example, a thread or mesh that secures the longitudinally extending member to the balloon. In other embodiments, a polymer matrix can be used to bond the longitudinally extending member to the surface of the balloon. In some embodiments, the medical balloon can be an angioplasty balloon. In some embodiments, the medical balloon can be an off-the-shelf medical balloon, such as an off-the-shelf angioplasty balloon.

A serration balloon can comprise an off-the shelf medical balloon, such as an angioplasty balloon, with a plurality of cutting blades along a surface of the medical balloon. Each cutting blade of the plurality of cutting blades can comprise a strip of material with periodic raised wedges spaced along a length thereof. The plurality of cutting blades can be secured to balloon surface by a polymer matrix. The polymer matrix can be positioned between the plurality of cutting blades and the balloon surface, while also being around each of the plurality of cutting blades. The polymer matrix can be applied to the balloon prior to securing the plurality of cutting blades to the balloon and then the same polymer matrix can be reapplied to secure the plurality of cutting blades in place.

In some embodiments, each cutting blade of the plurality of cutting blades is a flat, planar piece of material that has the periodic raised wedges cut out along a length of the material. The flat, planar piece of material defining a primary plane, and the periodic raised wedges being in plane with the primary plane of the flat, planar piece of material. The plurality of cutting blades can be positioned along the surface of the medical balloon in the inflated state such that the primary plane is perpendicular to the surface of the medical balloon where it is attached. The flat, planar piece of material can not have a base or flange or other feature that extends outward from the side of the flat, planar piece of material. In addition, the periodic raised wedges can be solid and non-hollow (i.e. non needle-like).

A method of manufacturing a serration balloon can comprise inflating a medical balloon, the medical balloon being on a catheter; dipping the medical balloon in the inflated state in a polymer matrix, such that the medical balloon has first layer of the polymer matrix; attaching a plurality of cutting blades along a surface of the medical balloon in the inflated state, each cutting blade of the plurality of cutting blades comprising a strip of material with periodic raised wedges spaced along a length thereof; and dipping the medical balloon in the inflated state with the attached plurality of cutting blades in the polymer matrix to form an over mold, such that at least a portion of each cutting blade of the plurality of cutting blades is sandwiched between the first layer of the polymer matrix and a second layer of the first polymer matrix.

A method of manufacturing a serration balloon can comprise inflating a medical balloon, the medical balloon being on a catheter; attaching a plurality of cutting blades along the surface of the medical balloon in the inflated state, each cutting blade of the plurality of cutting blades comprising a strip of material with periodic raised wedges spaced along a length thereof; and dipping the medical balloon in the inflated state with the attached plurality of cutting blades in a polymer matrix to form an over mold securing the plurality of cutting blades to the medical balloon.

A method of manufacturing a serration balloon can comprise inflating a medical balloon, the medical balloon being on a catheter; dipping the medical balloon in the inflated state in a polymer matrix to form a first layer of polymer matrix on an outer surface of the medical balloon; attaching a plurality of cutting blades to the first layer of polymer matrix along the surface of the medical balloon in the inflated state, each cutting blade of the plurality of cutting blades comprising a strip of material with periodic raised wedges spaced along a length thereof; and dipping the medical balloon in the inflated state with the attached plurality of cutting blades in the polymer matrix to form an over mold, a second layer of polymer matrix further securing the plurality of cutting blades to the first layer or polymer matrix and the medical balloon.

BRIEF DESCRIPTION OF THE DRAWINGS

Various embodiments are depicted in the accompanying drawings for illustrative purposes, and should in no way be interpreted, as limiting the scope of the inventions, in which like reference characters denote corresponding features consistently throughout similar embodiments.

DETAILED DESCRIPTION

Disclosed herein are various embodiments of systems and methods discussed primarily in the context of treating occlusive disease, including balloon angioplasty methods and systems. At the same time, it will be understood that the concepts and principles embodied in the various embodiments can also be used with other types of medical balloons, cutting balloons, and other types of medical procedures.

A cutting or serration balloon can have a number of different components and can be made in a number of different manners. For example, one or more longitudinally extending members with periodic raised wedges can be attached to a medical balloon. They can be attached with a fiber coating, a polymer coating, or other methods, various embodiments of which will be discussed below. The fiber coating can be, for example, a thread or mesh that secures the longitudinally extending member to the balloon. In other embodiments, a polymer matrix can be used to bond the longitudinally extending member to the surface of the balloon. In some embodiments, the medical balloon can be an angioplasty balloon. In some embodiments, the medical balloon can be an off-the-shelf medical balloon, such as an off-the-shelf angioplasty balloon.

Figure 1:
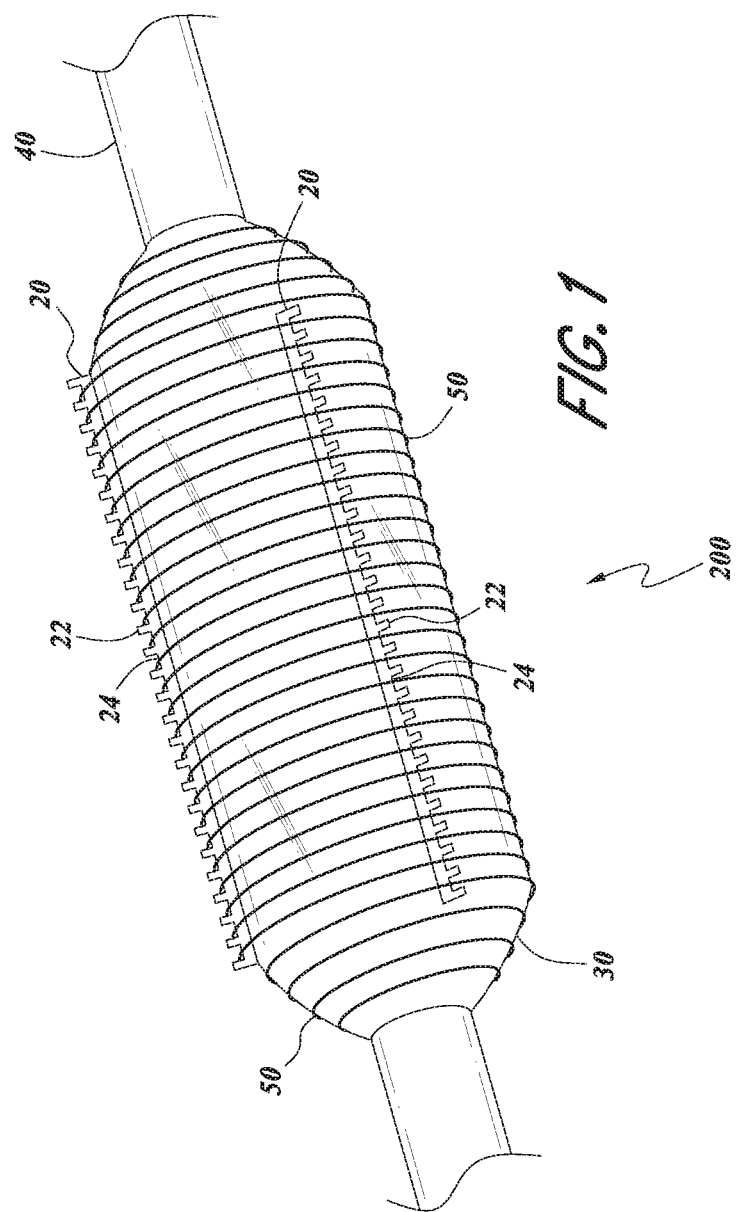
FIG. 1 is a perspective view of a cutting or serration balloon with a fiber coating in an inflated state.
Figure 2:
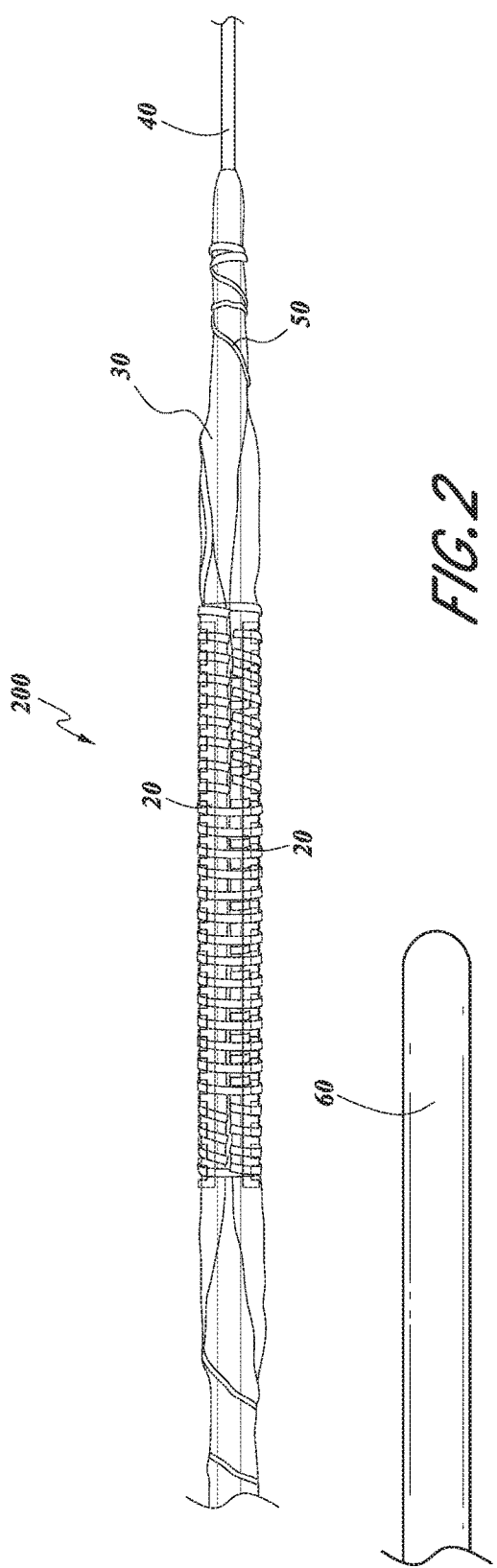
FIG. 2 shows a cutting or serration balloon with a fiber coating in a deflated state.

FIG. 1 shows a cutting or serration balloon with fiber coating 200 including a catheter 40, a balloon 30, at least one longitudinally extending member 20, and fiber 50. As seen in FIG. 1, in some embodiments, fiber 50 is a thread that is wound about the balloon 30 and the at least one longitudinally extending member 20. FIG. 2 shows the cutting balloon 200 in a deflated state. As can be seen, the balloon 30 can be wrapped around the catheter 40. A sheath 60 can also be used to secure the balloon in the deflated state prior to expansion.

Figure 3:
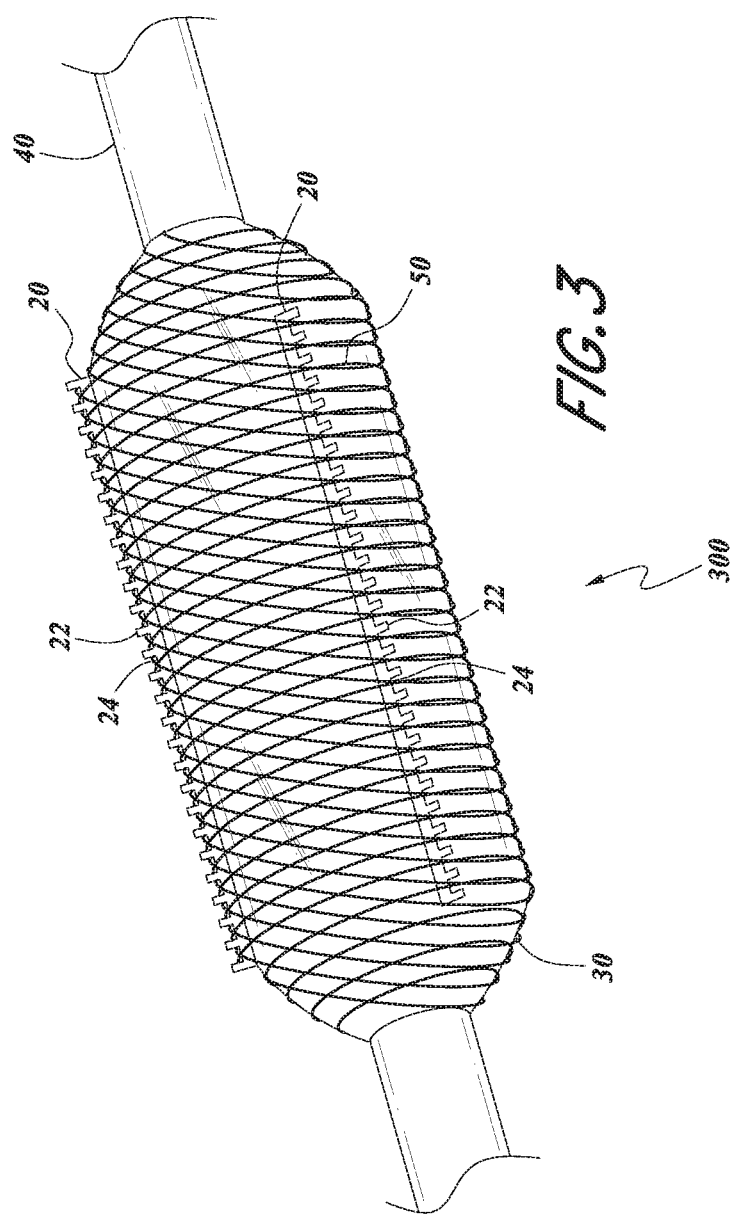
FIG. 3 shows another cutting or serration balloon with fiber coating.

FIG. 3 shows a similar cutting balloon with fiber coating 300 wherein the fiber 50 forms a mesh. In some embodiments, a cutting balloon with fiber coating 200, 300 can include at least one radiopaque marker (not pictured). The at least one radiopaque marker is located on the catheter 40 to assist with placement and identification of the balloon 30 in the body.

FIG. 3 provides a view of the balloon 30 and at least one longitudinally extending member 20 without the fiber 50. FIG. 3 shows a cutting balloon without the fiber coating 200 and including a catheter 40, a balloon 30, and at least one longitudinally extending member 20. The balloon 30 can be attached to the catheter 40 and each of the longitudinally extending members 20 are attached to the surface of the balloon 30.

Figures 4, 6:
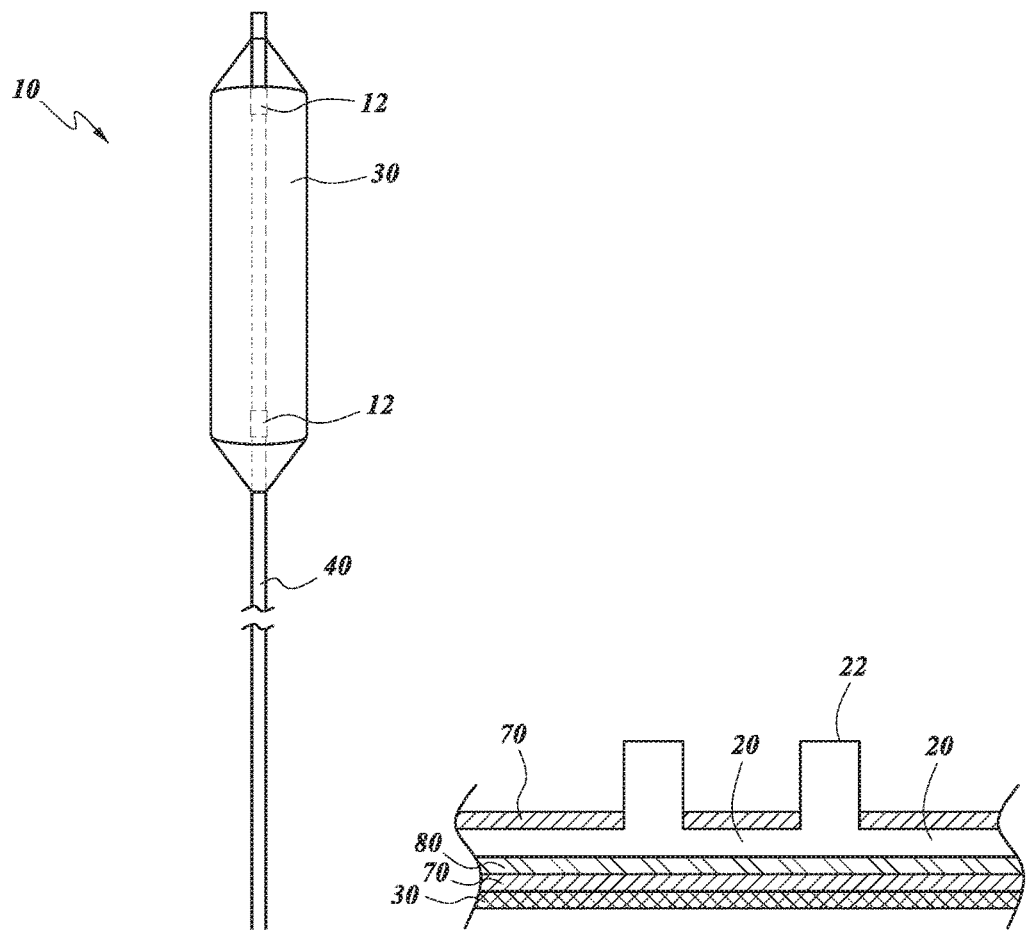
FIG. 4 illustrates a catheter balloon.
FIG. 6 is a cross-sectional detail view of a cutting or serration balloon.

FIG. 4 shows a catheter balloon 10. The illustrated catheter balloon 10 can be an off-the-shelf medical balloon, such as an angioplasty balloon. The catheter balloon 10 can be used to create a serration or cutting balloon. As shown, the catheter balloon has a catheter shaft 40 with a balloon 30 at the distal end. Radiopaque markers 42 are shown positioned inside the balloon 30. The shaft 40 can be hollow and can be used to inflate the balloon and can also be used with a guidewire. Thus, as shown, the shaft 40 can have two channels, one for inflation and one for positioning with a guidewire. A hub 44 is shown with two entry points for the shaft 40 and can be a y-hub and strain relief.

In some embodiments the catheter can be a coaxial over-the-wire balloon catheter with a guidewire size compatibility of 0.018". A high pressure (non-compliant/semi-compliant) trifold balloon can be made of nylon material with a diameter of 5 mm and a length of 20 mm ±1 mm. The balloon has a nominal inflation pressure of 10 atm, a rated burst pressure of 22 atm, and an average burst pressure of 22 atm. The catheter working length is 110 cm ±2 cm and has a tapered tip length of 3 mm ±0.5 mm. Two standard radiopaque makers 42 are made up of 90% platinum and 10% iridium. The radiopaque markers 42 indicate the balloon working length. The inner shaft has a lubricious HDPE inner layer. The profile of the outer shaft is clear and 4.3FR (0.056 in ±0.0008 in; 1.42 mm ±0.0200 mm.

The balloon 30 is disposed about the catheter 40 and is capable of being inflated. In some embodiments the balloon 30 is disposed about the distal end of the catheter 40 to be used in balloon angioplasty. In balloon angioplasty, the balloon can be inflated in order to mechanically widen or narrow obstructed arteries from plaque or other related deposits in the lumen of the blood vessel. As will be described below in more detail, structures can be attached to the surface of the balloon 30 that can be used to cut or score the plaque as the balloon 30 is expanded. Such an expansion opens up the blood vessel for improved flow. Subsequent to this procedure, the balloon 30 can be deflated and withdrawn from the body. In some embodiments, the balloon is a high pressure balloon. In some embodiments, the balloon 30 is made of nylon, has a diameter of 5 mm and can withstand a pressure of up to 22 atm.

Longitudinally extending members 20 can be positioned about the balloon 30. Each of the longitudinally extending members 20 include a plurality of periodic raised wedges 22 that are spaced apart by a plurality of grooves 24. The periodic raised wedges can have a height between 100 um to 500 um, more commonly between 150 um and 300 um, and frequently between 200 um and 250 um. The periodic raised wedges 22 extend longitudinally along the longitudinally extending members 20 each with a length that can be between 100 um to 1 mm, more commonly between 350 um and 750 um, and frequently between 400 um and 550 um. While the plurality of grooves 24 can extend longitudinally along the longitudinally extending members 20 each with a length that is between 1 times to 3 times the length of the periodic raised wedges 22, that can be between 100 um to 3 mm, more commonly between 350 um and 2 mm, and frequently between 800 um and 1.2 mm. In the illustrated embodiments, the longitudinally extending members 20 are strips of metal with rectangular shapes cut perpendicular to the length of the strips with a laser, EDM, grinding wheel, or similar to form the periodic raised wedges 22 and grooves 24. In some embodiments, the longitudinally extending members 20 can be in the form of strips, wires, ribbons, fibers, splines, etc. The periodic raised wedges 22 and grooves 24 can also vary in size and shape. In some embodiments, the periodic raised wedges 22 can have a height of 0.01 inches. In some embodiments, the periodic raised wedges 22 can be pointed, rounded, trapezoidal or can be shaped protrusions attached to the surface of the longitudinally extending members 20. The strips of metal can be flat, rounded, trapezoidal, or triangular in cross section.

The longitudinally extending members 20 can be attached to the balloon in a number of different ways. For example the longitudinally extending members 20 can be glued to the balloon. The longitudinally extending members 20 can be attached with a fiber, a polymer matrix, or other material.

In some embodiments, each longitudinally extending member 20 is a flat, planar piece of material that has the periodic raised wedges 22 cut out along a length of the material. The flat, planar piece of material defining a primary plane, and the periodic raised wedges being in plane with the primary plane of the flat, planar piece of material. The longitudinally extending members 20 can be positioned along the surface of the medical balloon in the inflated state such that the primary plane is perpendicular to the surface of the medical balloon where it is attached. For example, that longitudinally extending members 20 can be positioned to be aligned with the longitudinal axis of the catheter and the balloon. The flat, planar piece of material can not have a base or flange or other feature that extends outward from the side of the flat, planar piece of material. In addition, the periodic raised wedges can be solid and non-hollow (i.e. non-needle-like).

As shown in FIGS. 1-3 a fiber 50 can be used to attach the longitudinally extending members 20 to the balloon. The fiber 50 is disposed about the surface of the balloon 40 and the longitudinally extending members 20. The fiber 50 can come in a variety of forms. In one embodiment, as seen in FIG. 1, the fiber 50 is in the form of a thread that is wound about the surface of the balloon 30 and the longitudinally extending members 20. In some embodiments, the thread can be constructed of a variety of materials which include metal, plastic, natural fibers, etc. The thread can be of any number of different constructions including, single strand, multi-strand, a coating or series of strands around a core, etc. In another embodiment, as seen in FIG. 3, the fiber 50 is in the form of a mesh that is disposed about the balloon 30 and the longitudinally extending members 20. The mesh can be made of the same types of materials as the thread. In some embodiments the mesh can be constructed of a variety of materials which include metal, plastic, natural fibers, etc. In some embodiments, the fiber 50 can be a variety of thicknesses and shapes and can take on a number of configurations such as woven, knitted, knotted, etc.

The cutting balloon with fiber coating 200 can be created in a number of ways. For example in some embodiments, the balloon 30 is first brought to an expanded state. This can be done by inflating the balloon. Once the balloon 30 is expanded, the longitudinally extending members 20 are placed about the surface of the expanded balloon and secured to the balloon by the fiber 50. In the embodiment pictured in FIG. 1, the fiber 50 is a thread and wound about the surface of the balloon 30 and the grooves 24 of the longitudinally extending members 20. In another example, in the embodiment pictured in FIG. 2, the fiber 50 is a mesh that is secured to the balloon 30 on the proximal and distal ends of the balloon 30. The intersecting fibers of the mesh engage with the grooves 24 of the longitudinally extending members 20. The combined structure of the expanded balloon 30, longitudinally extending members 20, and fiber 50 is then covered in an adhesive mixture or polymer matrix as described below. The balloon 30 can then be deflated prior to insertion into the patient. After manufacturing, the cutting balloon with fiber coating 200 can be covered with a balloon protector or sheath 60 that can be made of, for example, PTFE. As well, the cutting balloon with fiber coating 200 can be further packaged by placing the cutting balloon into a coiled hoop and then placed into a re-closeable bag in a carton. The sheath 60 can helps to prevent the periodic raised wedges 22 of the longitudinally extending members 20 from unintentional contact with the patient as it is inserted.

A cutting balloon can include longitudinally extending members 20, balloon 30, catheter 40 and fiber 50 discussed above. In some embodiments, the balloon 30 is located on the distal end of the catheter 40. In some embodiments, the fiber 50 is only wrapped about the balloon 30 and spans from the proximal end of the balloon 30 to the distal end of the balloon 30.

In some embodiments, the cutting balloon has three longitudinally extending members 20 that are equally spaced radially around the balloon 30. The longitudinally extending members 20 can be attached to the flat surface of the balloon 30. The fiber 50 is a thread that is wrapped about the longitudinally extending members 20 and secures each of the longitudinally extending members 20 to the surface of the balloon 30 by securing the grooves 24 that are located between each of the periodic raised wedges 22 on the longitudinally extending members 20.

Once the cutting balloon with fiber coating 200 is inserted into the body of a patient and navigated to the target site, the balloon 30 can be expanded in a controlled fashion so that the longitudinally extending members 20 can be pushed against the walls of the lumen surface. The balloon 30 can be controllably inflated to increase its diameter. As the balloon 30 is inflated, the attached longitudinally extending members 20 are pushed outwards against the lumen. The periodic raised wedges 22 of the longitudinally extending members 20 can engage with the plaque in the lumen walls when the balloon 30 is expanded.

Other manufacturing methods can also he used. For example, the longitudinally extending members 20 can be sandwiched between two balloons. Such devices may or may not also include fibers 50. In another method, the longitudinally extending members 20 can be secured to the balloon during the balloon molding process. Further, the polymer material used to form the balloon can also be used to form the fiber 50. The balloon and fiber can be cured together with the longitudinally extending members 20 installed.

Figure 5:
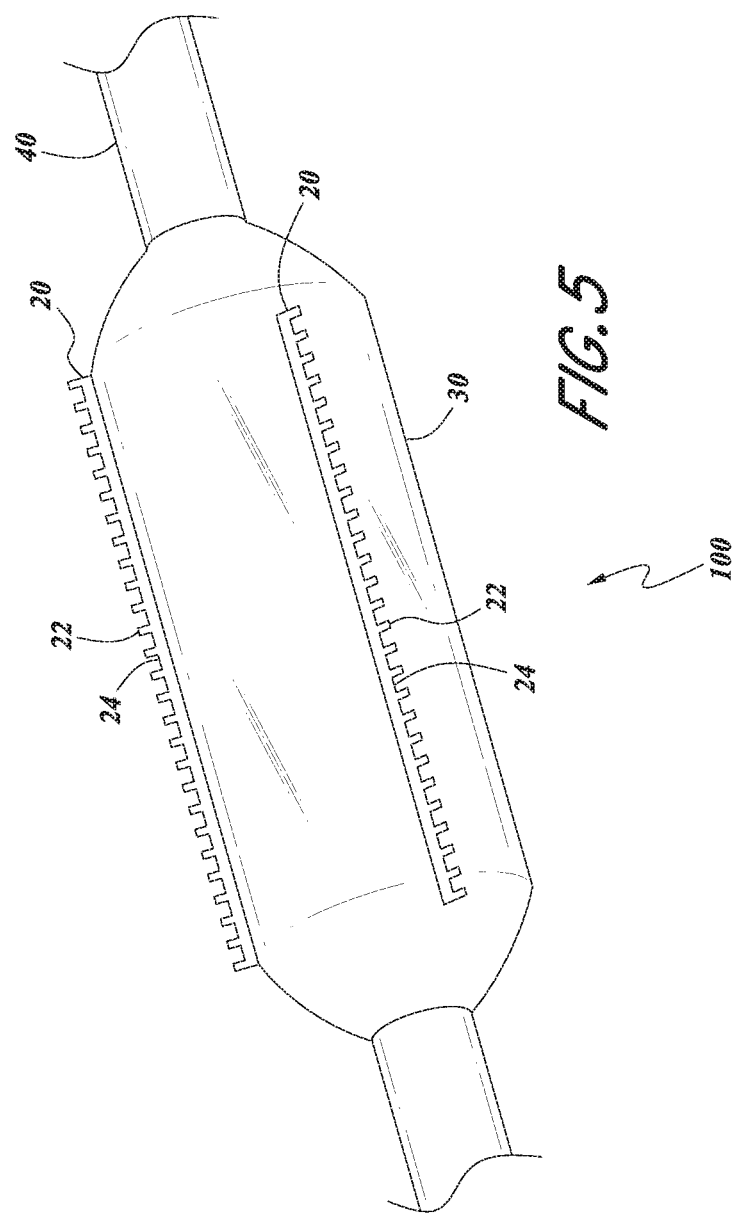
FIG. 5 shows an embodiment of a cutting or serration balloon.

Turning now to FIG. 5, another embodiment of serration or cutting balloon 100 will be discussed. FIG. 5 provides a view of the balloon 30 and at least one longitudinally extending member 20 that has been over molded. To achieve an over mold one method is to immerse the inflated balloon 30 into a solution such as a polymer matrix. The polymer matrix can be at least one of a urethane, nylon, silicon, or alternate elastomeric material designed to offer flexibility while offering good adhesion, cohesion and biocompatibility properties. These materials can be hydrophilic, hydrated or non-hydrated, UV curable, and/or dissolvable in organic or inorganic solvents. It will also be understood that the polymer matrix can comprise one or more different polymer matrixes, where for example the balloon is dipped in a particular order.

The balloon 30 can be dipped and then remain immersed in a solution for a given amount of time to allow a thin layer to deposit itself on the balloon. The balloon 30 with the coating can be allowed to drain and the solvent to evaporate. Then the balloon can be dipped again multiple times until an adequate layer is achieved. The longitudinally extending members 20 can then be attached to the balloon, followed by additional dipping into the polymer matrix. This can secure the longitudinally extending members 20 to the balloon with layers of the polymer matrix forming a strong bond to the balloon and the longitudinally extending members 20.

In some embodiments to aid the over mold in retention of the longitudinally extending members 20 to the balloon 30, the longitudinally extending members 20 can be dipped into the polymer matrix prior to attaching the longitudinally extending members 20 to the balloon. This may be in addition to or instead of bonding the longitudinally extending members 20 to the coated balloon with an adhesive material. Adhesive bonding to the coated balloon can be achieved with one or more points of attachment or along the entire length of the longitudinally extending members 20. After the longitudinally extending members 20 are affixed to the coated balloon surface a series of additional dips can be performed to achieve an affective retention layer. Since the longitudinally extending members 20 contain a series of recesses 24 between the periodic raised wedges 22 of metal, a backbone or strip of material can be identified offering a surface platform that the over mold or polymer coating can flow over and form a blanket or second layer of balloon to retain the longitudinally extending members 20.

FIG. 6 shows a cross-sectional detail view of a serration balloon. The balloon 30 is shown with two layers of polymer matrix 70, an adhesive layer 80 and a longitudinally extending member 20. As illustrated it can be seen that the longitudinally extending member 20 is sandwiched between layers of the polymer matrix 70. The polymer matrix 70 may or may not cover the wedges 2.

Whether the additive material is fiber, mesh, dip/s, second balloon, or strip/s of material added to the outside of the balloon, the material on the outside of the balloon may be completely or selectively doped with a drug or STEM cell matrix through a series of surface ionic bonding manipulation. One such method of surface ionic bonding manipulation is performed by exposing the additive material to an environment with a selected ionic charge. Following selected ionic charging of the balloon surface the balloon can then be exposed to an alternate charge dopant filled environment to be adhered to the surface by ionic bonding energies. This process is repeatable until a suitable layer of desired dopant/s is achieved. A photolithographic process or other selective process such as templated assembly of selective removal may be employed.

The balloon 30 with the over mold can also be doped with a drug or STEM cell matrix through a series of surface ionic bonding manipulation. One such method of surface ionic bonding manipulation is performed by exposing the balloon 30 to an environment with a selected ionic charge. Following selected ionic charging of the balloon surface the balloon can then be exposed to an alternate charge dopant filled environment to be adhered to the surface by ionic bonding energies. This process is repeatable until a suitable layer of desired dopant/s is achieved.

A serration balloon can comprise an off-the shelf medical balloon, such as an angioplasty balloon, with a plurality of cutting blades along a surface of the medical balloon. Each cutting blade of the plurality of cutting blades can comprise a strip of material with periodic raised wedges spaced along a length thereof. The plurality of cutting blades can be secured to balloon surface by a polymer matrix. The polymer matrix can be positioned between the plurality of cutting blades and the balloon surface, while also being around each of the plurality of cutting blades. The polymer matrix can be applied to the balloon prior to securing the plurality of cutting blades to the balloon and then the same polymer matrix can be reapplied to secure the plurality of cutting blades in place.

A method of manufacturing a serration balloon can comprise inflating a medical balloon, the medical balloon being on a catheter; dipping the medical balloon in the inflated state in a polymer matrix, such that the medical balloon has first layer of the polymer matrix; attaching a plurality of cutting blades along a surface of the medical balloon in the inflated state, each cutting blade of the plurality of cutting blades comprising a strip of material with periodic raised wedges spaced along a length thereof; and dipping the medical balloon in the inflated state with the attached plurality of cutting blades in the polymer matrix to form an over mold, such that at least a portion of each cutting blade of the plurality of cutting blades is sandwiched between the first layer of the polymer matrix and a second layer of the first polymer matrix.

The method can further comprises applying an adhesive material to a bottom surface of each cutting blade of the plurality of cutting blades prior to attaching the plurality of cutting blades along the surface of the medical balloon. The method can further comprise dipping each cutting blade of the plurality of cutting blades into the polymer matrix prior to dipping the medical balloon with the attached plurality of cutting blades in the polymer matrix. Applying an adhesive material to a bottom surface of each cutting blade of the plurality of cutting blades prior to attaching the plurality of cutting blades along the surface of the medical balloon and after dipping each cutting blade of the plurality of cutting blades into the polymer matrix.

A method of manufacturing a serration balloon can comprise inflating a medical balloon, the medical balloon being on a catheter; attaching a plurality of cutting blades along the surface of the medical balloon in the inflated state, each cutting blade of the plurality of cutting blades comprising a strip of material with periodic raised wedges spaced along a length thereof; and dipping the medical balloon in the inflated state with the attached plurality of cutting blades in a polymer matrix to form an over mold securing the plurality of cutting blades to the medical balloon.

In some embodiments, the cutting blades can comprise strips of metal with a plurality of identical periodic raised wedges spaced along a length thereof, the periodic raised wedges not being hollow. The method can further comprise forming each cutting blade of the plurality of cutting blades from a flat, planar piece of material by cutting out the periodic raised wedges along a length of the material, the flat, planar piece of material defining a primary plane, and the periodic raised wedges being in plane with the primary plane of the flat, planar piece of material. Attaching the plurality of cutting blades along the surface of the medical balloon in the inflated state can further comprise attaching each cutting blade such that the primary plane is perpendicular to the surface of the medical balloon where it is attached. The flat, planar piece of material can not have a base or flange or other feature that extends outward from the side of the flat, planar piece of material.

A serration balloon can comprise an off-the shelf medical balloon, such as an angioplasty balloon, with a plurality of cutting blades along a surface of the medical balloon. Each cutting blade of the plurality of cutting blades can comprise a strip of material with periodic raised wedges spaced along a length thereof. The plurality of cutting blades can be secured to balloon surface by a polymer matrix. The polymer matrix can be positioned between the plurality of cutting blades and the balloon surface, while also being around each of the plurality of cutting blades. The polymer matrix can be applied to the balloon prior to securing the plurality of cutting blades to the balloon and then the same polymer matrix can be reapplied to secure the plurality of cutting blades in place.

In some embodiments, each cutting blade of the plurality of cutting blades is a flat, planar piece of material that has the periodic raised wedges cut out along a length of the material. The flat, planar piece of material defining a primary plane, and the periodic raised wedges being in plane with the primary plane of the flat, planar piece of material. The plurality of cutting blades can be positioned along the surface of the medical balloon in the inflated state such that the primary plane is perpendicular to the surface of the medical balloon where it is attached. The flat, planar piece of material can not have a base or flange or other feature that extends outward from the side of the flat, planar piece of material. In addition, the periodic raised wedges can be solid and non-hollow (i.e. non-needle-like).

A serration balloon can include an off-the shelf medical balloon; a plurality of cutting blades along a surface of the medical balloon, each cutting blade of the plurality of cutting blades comprising a strip of material with periodic raised wedges spaced along a length thereof; and a multi-layer polymer matrix, the plurality of cutting blades secured to the balloon surface by the multi-layer polymer matrix, the multi-layer polymer matrix positioned between the plurality of cutting blades and the balloon surface, while also being around each of the plurality of cutting blades. The polymer matrix can be applied to the balloon prior to securing the plurality of cutting blades to the balloon and then the same polymer matrix (or combination of polymer matrixes) can be reapplied to secure the plurality of cutting blades in place.

A benefit of the controlled balloon expansion system is it can allow for control of the angle of energy departed to the surface of the body lumen. According to some embodiments, this may be achieved through control of the depth of longitudinally extending members or the diameter at which the constrained balloon makes contact with the lumen wall. With a controlled depth of the longitudinally extending members, an angular depression can he generated along the lumen axis of the balloon that can apply a tangential force against the lumen wall at an angle of 45 degrees or less perpendicular to the lumen axis. At this angle the lumen tissue is susceptible to separating along the mid line of the depressed region. It can be noted that when attempting to tear a 2-D surface it is observed that an angle less than 90 degrees exists and offers greater control for predetermining the tear location and reduces the energy required to start and facilitate the continuation of a tear in the 2-D surface of many materials. When inducing expansion of arteries or other lumen tissue it is observed that the angle of energy departed at the lumen surface has an expansion effect at a similar angle to that as observed in the 2-D surface example. It has been observed that angles equal to or less than 45 degrees appear to have beneficial tearing effects on plaque in a blood vessel, although other predetermined angles may be used when tissue expansion is not the only desired effect.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. In addition, while a number of variations of the invention have been shown and described in detail, other modifications, which are within the scope of this invention, will be readily apparent to those of skill in the art based upon this disclosure. It is also contemplated that various combinations or sub-combinations of the specific features and aspects of the embodiments may be made and still fall within the scope of the invention. Accordingly, it should be understood that various features and aspects of the disclosed embodiments can be combined with or substituted for one another in order to form varying modes of the disclosed invention. Thus, it is intended that the scope of the present invention herein disclosed should not be limited by the particular disclosed embodiments described above, but should be determined only by a fair reading of the claims that follow.

Similarly, this method of disclosure, is not to he interpreted as reflecting an intention that any claim require more features than are expressly recited in that claim. Rather, as the following claims reflect, inventive aspects lie in a combination of fewer than all features of any single foregoing disclosed embodiment. Thus, the claims following the Detailed Description are hereby expressly incorporated into this Detailed Description, with each claim standing on its own as a separate embodiment.

What is claimed is:

1. A method of manufacturing a serration balloon, comprising:
   inflating a medical balloon, the medical balloon being on a catheter;
   dipping the medical balloon in the inflated state in a polymer matrix, such that the medical balloon has first layer of the polymer matrix;
   attaching a plurality of cutting blades along a surface of the medical balloon in the inflated state, each cutting blade of the plurality of cutting blades comprising a strip of material with periodic raised wedges spaced along a length thereof; and
   dipping the medical balloon in the inflated state with the attached plurality of cutting blades in the polymer matrix to form an over mold, such that at least a portion of each cutting blade of the plurality of cutting blades is sandwiched between the first layer of the polymer matrix and a second layer of the first polymer matrix.

2. The method of claim 1, wherein dipping the medical balloon comprises dipping an off-the-shelf angioplasty balloon in the polymer matrix.

3. The method of claim 1, wherein the polymer matrix comprises at least one of urethane, nylon, and silicon.

4. The method of claim 1, further comprising draining excess of the polymer matrix from the medical balloon.

5. The method of claim 4, further comprising allowing a solvent from the polymer matrix to evaporate.

6. The method of claim 1, further comprising applying an adhesive material to a bottom surface of each cutting blade of the plurality of cutting blades prior to attaching the plurality of cutting blades along the surface of the medical balloon.

7. The method of claim 1, further comprising dipping each cutting blade of the plurality of cutting blades into the polymer matrix prior to dipping the medical balloon with the attached plurality of cutting blades in the polymer matrix.

8. The method of claim 7, further comprising applying an adhesive material to a bottom surface of each cutting blade of the plurality of cutting blades prior to attaching the plurality of cutting blades along the surface of the medical balloon and after dipping each cutting blade of the plurality of cutting blades into the polymer matrix.

9. The method of claim 1, further comprising doping the medical balloon with the attached plurality of cutting blades and the over mold with a drug or STEM cell matrix.

10. The method of claim 9, wherein doping further comprises exposing the balloon to an environment with a selected ionic charge and then exposing the balloon to an alternate charge dopant filled environment.

11. The method of claim 1, wherein the cutting blades comprise strips of metal with a plurality of identical periodic raised wedges spaced along a length thereof, the periodic raised wedges not being hollow.

12. The method of claim 1, wherein the periodic raised wedges each have a height between 100 um to 500 um, 150 um and 300 um, and 200 um and 250 um.

13. The method of claim 12, wherein the periodic raised wedges each have a length between 100 um to 1 mm, 350 um and 750 um, and 400 um and 550 um.

14. The method of claim 13, wherein the periodic raised wedges are based apart by a plurality of grooves, each groove being 1 times to 3 times the length of at least one of the periodic raised wedges.

15. The method of claim 13, wherein the periodic raised wedges are based apart by a plurality of grooves, each groove having a length of between 100 um to 3 mm, 350 um and 2 mm, and 800 um and 1.2 mm.

16. The method of claim 1, further comprising forming each cutting blade of the plurality of cutting blades from a flat, planar piece of material by cutting out the periodic raised wedges along a length of the material, the flat, planar piece of material defining a primary plane, and the periodic raised wedges being in plane with the primary plane of the flat, planar piece of material.

17. The method of claim 1, wherein attaching the plurality of cutting blades along the surface of the medical balloon in the inflated state further comprises attaching each cutting blade such that the primary plane is perpendicular to the surface of the medical balloon where it is attached.

18. The method of claim 17, wherein there the flat, planar piece of material does not have a base or flange or other feature that extends outward from the side of the flat, planar piece of material.

19. The method of claim 1, wherein the polymer matrix comprises a first polymer matrix and a second polymer matrix and the steps of dipping the medical balloon into the polymer matrix comprises dipping the medical balloon into the first polymer matrix followed by dipping the balloon into the second polymer matrix.

20. A method of manufacturing a serration balloon, comprising:
    inflating a medical balloon, the medical balloon being on a catheter;
    dipping the medical balloon in the inflated state in a polymer matrix to form a first layer of polymer matrix on an outer surface of the medical balloon;
    attaching a plurality of cutting blades to the first layer of polymer matrix along the surface of the medical balloon in the inflated state, each cutting blade of the plurality of cutting blades comprising a strip of material with periodic raised wedges spaced along a length thereof; and
    dipping the medical balloon in the inflated state with the attached plurality of cutting blades in the polymer matrix to form an over mold, a second layer of polymer matrix further securing the plurality of cutting blades to the first layer or polymer matrix and the medical balloon.

\* \* \* \* \*